United States Patent [19]

Paul

[11] Patent Number: 4,988,199

[45] Date of Patent: Jan. 29, 1991

[54] METHOD AND APPARATUS FOR MEASURING THE CONCENTRATION OF OPTICALLY ACTIVE SUBSTANCES

[75] Inventor: Bernt-Joachim Paul, Erlangen, Fed. Rep. of Germany

[73] Assignee: Siemens Aktiengesellschaft, Berlin & Munich, Fed. Rep. of Germany

[21] Appl. No.: 382,841

[22] Filed: Jul. 19, 1989

[30] Foreign Application Priority Data

Jul. 19, 1988 [DE] Fed. Rep. of Germany ....... 3824589

[51] Int. Cl.⁵ ............................................. G01N 21/21
[52] U.S. Cl. ..................................... 356/368; 250/225
[58] Field of Search .................. 356/367, 368; 250/225

[56] References Cited

U.S. PATENT DOCUMENTS 3,397,607 8/1968 Goodwin .

FOREIGN PATENT DOCUMENTS

| 1121357 | 1/1962 | Fed. Rep. of Germany . |
| 2734391 | 2/1979 | Fed. Rep. of Germany . |
| 2944113 | 5/1981 | Fed. Rep. of Germany . |
| 0882244 | 11/1961 | United Kingdom . |
| 2197467 | 5/1988 | United Kingdom . |
| 8803266 | 5/1988 | World Int. Prop. O. .......... 356/368 |

OTHER PUBLICATIONS

Rogouoi et al., "High-precision polarimeter-saccharimeter for an automatic testing line", *Sov. J. Opt. Technol.* vol. 47, No. 5, pp. 276–278, 5/1980.

Gates et al, "An Automatic Recording Saccharimeter", *Chemestry and Industry*, pp. 190–193, 2/1958.

Optics and Spectroscopy, vol. 32, No. 6, Jun. 1972, pp. 667–669; A. V. Malakhovskii: "Automatic Spectropolarimeter" (no date).

*Primary Examiner*—Davis L. Willis
*Assistant Examiner*—Matthew W. Koren
*Attorney, Agent, or Firm*—Kenyon & Kenyon

[57] ABSTRACT

The concentration of optically active substances is determined by measuring the polarization of light passed through the substance using a light source, a polarizer and a modulator operated at a predetermined modulation frequency $f_F$, as well as a measuring cell, an analyzer and a detector. The output signal from the detector 16 is alternately integrated during each half period of the modulation frequency to form voltage values $U_{I+}$ and $U_{I-}$. These voltage values are stored and the quotient Q of these stored voltage values is formed. Subsequently, an adjustable constant voltage is subtracted from the quotient. The measuring arrangement can have a miniature design for implantation. No mechanically moving parts and only a single detector are used. The measurement is accomplished by a simple, miniature linear ray path having high resolution.

38 Claims, 4 Drawing Sheets

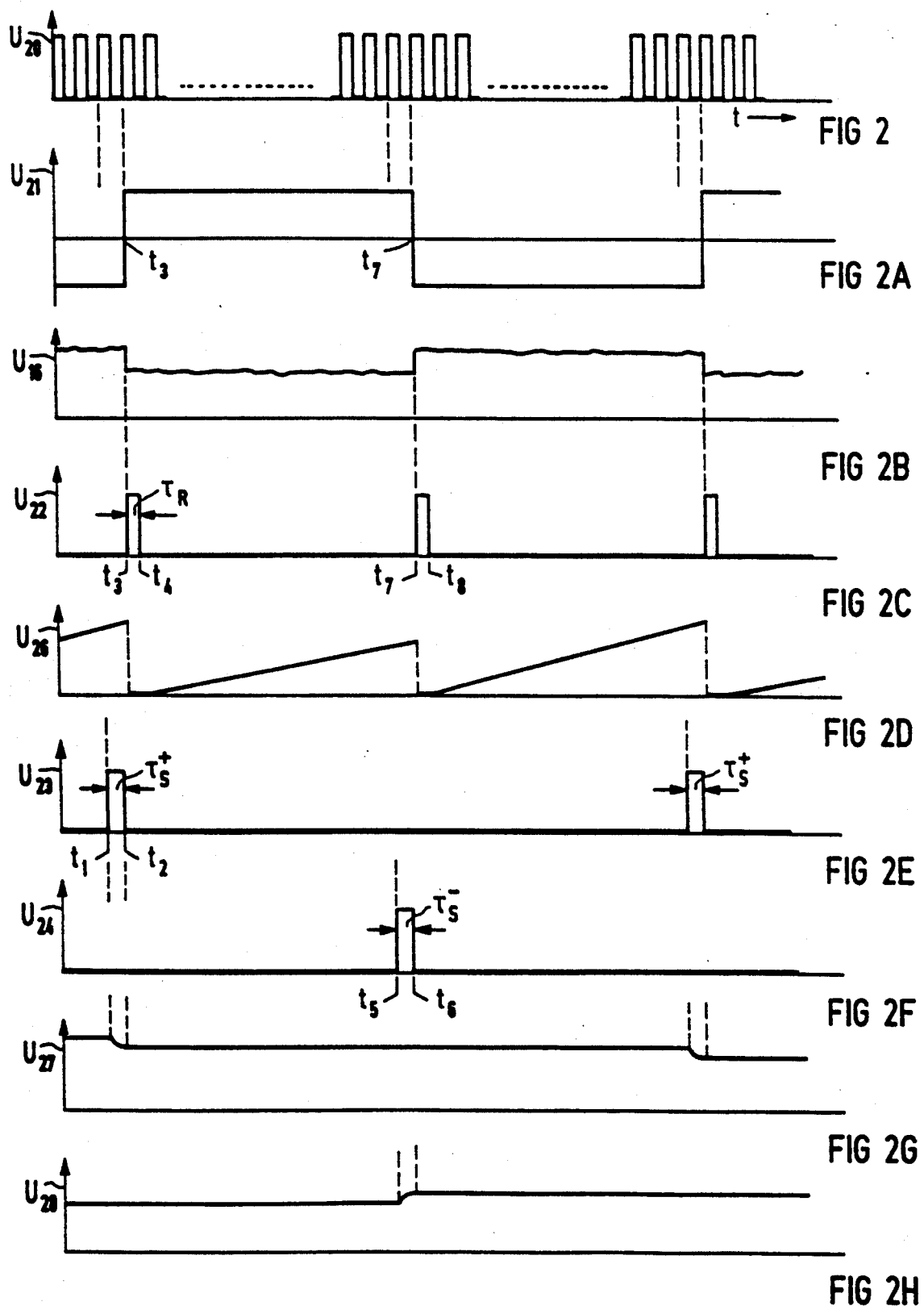

METHOD AND APPARATUS FOR MEASURING THE CONCENTRATION OF OPTICALLY ACTIVE SUBSTANCES

FIELD OF THE INVENTION

The invention relates to polarimeters for measuring the concentration of optically active substances and, more particularly, polarimeters which can be used to measure the glucose concentration in body liquids. The apparatus measures the polarization of polarized light fed to a detector through the substance to be analyzed. The polarized light passes through a modulator which is operated at a predetermined modulation frequency. From the modulator, the light passes through a measuring cell, which contains the substance, and an analyzer before reaching the detector.

BACKGROUND OF THE INVENTION

A prior known polarimeter operates in accordance with the principle of automatic optical null balance. The prior polarimeter contains two line radiators, a mercury and a sodium vapor lamp, as well as five optical filters arranged on a filter wheel. A tilting mirror is coupled to the filter wheel shaft. The mirror allows the radiation of the corresponding light source to be inserted into the ray path of the polarimeter at the same time the measuring wavelength is selected. Further, a quartz-iodine and a deuterium lamp are provided to furnish continuous radiation. A grid monochromator is provided to select the desired wavelength.

In this known design, the monochromatic light travels through the polarizer, the cell containing the sample, and the analyzer before arriving at a photo multiplier. The polarizer and analyzer are formed by rotatably arranged "glan" prisms made of calcite. The polarizer, including the respective plane of polarization of the transmitted light, vibrates about the optical longitudinal axis of the system at an excursion of about $\pm 0.7$ radians at 50 Hz. The 50 Hz signal is generated in the photo multiplier, in the unbalanced state of the system. The 50 Hz signal is amplified and fed, with the correct sign, to the power input of a servo motor. The servo motor is mechanically coupled to the analyzer for rotating the analyzer until the 50 Hz signal becomes zero.

An optically active sample inserted into the ray path causes rotation of the plane of polarization. The analyzer is turned by means of the servo system into the new balanced position. The angular difference between the new and the original balanced position corresponds to the optical capability of rotation of the sample. This type of apparatus, such as the Perkin Elmer model 241 MC, requires mechanical movement of the polarizer, a mechanically acting modulator and a motor rotated analyzer thus making the device unsuitable for miniaturization and/or implantation.

A further prior known method for determining the blood glucose using polarimetry operates by feeding polarized light via a Faraday modulator, operated at a predetermined modulation frequency, through the sample and an analyzer to the detector. In this known method, a further detector is provided because the ray is divided into both measuring and reference signals. Subsequently, the quotient is formed from the two output signals. However, methods using ray division, such as that shown in German Patent DE-OS No. 2944113, require suitable outlays for the optical system. Particularly, the two detectors must meet synchronization requirements.

There is therefore a need for a method and apparatus for measuring the concentration of optically active substances while allowing miniaturization and consequently, implantation into a living body.

SUMMARY OF THE INVENTION

The present invention solves this problem through the use of clocked, integrated signal processing in conjunction with a modulator and a single ray path to obtain a resolution of $5 \times (10^{-4})$ for an angle of rotation $\alpha_M$ of the plane of polarization. The apparatus of the present invention further operates without the use of any moving parts. For example, a relative resolution of 4% is obtained for a cell length of 2.7 cm and a resolution for a glucose concentration C of 34 mg/l (referred to the physiological standard value $C_0 = 800$ mg/l).

BRIEF DESCRIPTION OF THE DRAWINGS

FIGS. 2–2H are diagrams serving to explain the operation of FIG. 1.

DETAILED DESCRIPTION

Figure 1:
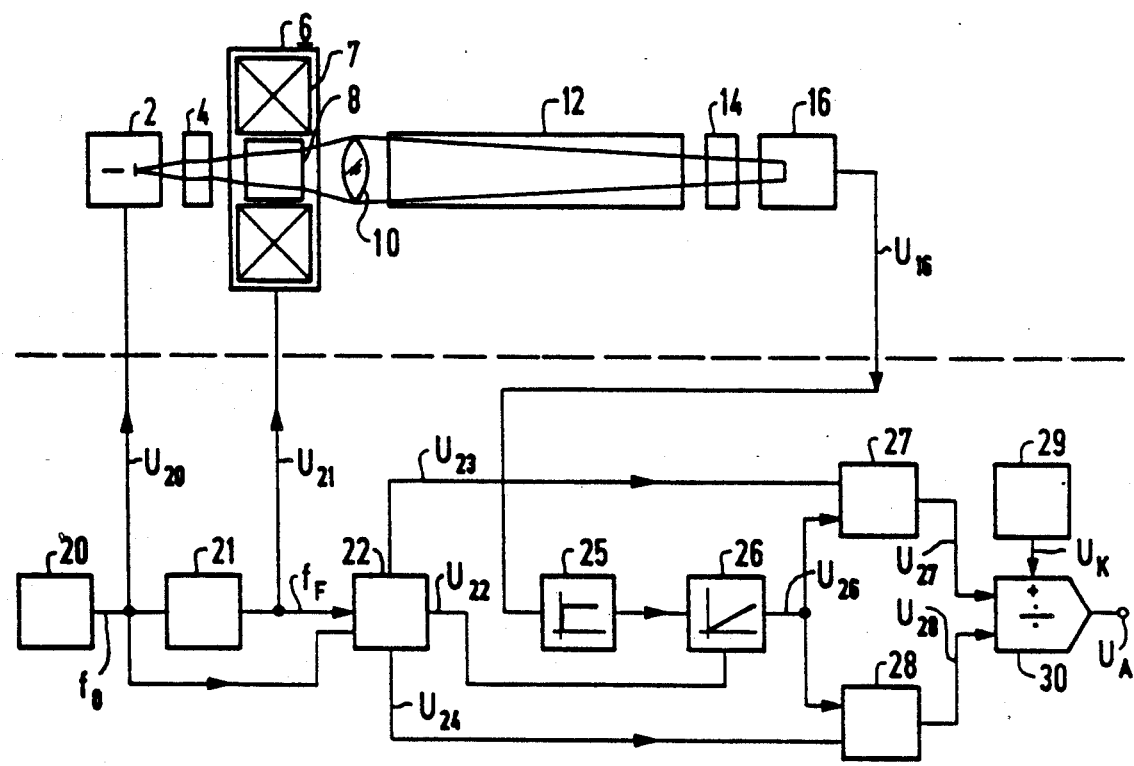
FIG. 1 schematically illustrates the design and the circuit for carrying out the method of the present invention.

Referring to FIG. 1, there is shown an apparatus for carrying out the method of determining the glucose concentration in body liquids, particularly in blood serum. A light source 2, preferably a light-emitting diode LED, emits light which passes through a polarizer 4, and a modulator 6 such as a Faraday modulator. This modulator 6 includes a coil 7 and a crystal 8. The apparatus further includes a lens 10 which may, for example, be made of glass or plastic, a measuring cell 12 for containing a liquid substance to be measured, an analyzer 14 and a detector 16. In the measuring cell 12, the plane of vibration of the light is rotated by an angle $\alpha_M$ because of the optically active substance (not shown). The light is at least approximately linearly polarized. The analyzer is adjusted to a permeability minimum with the modulator 6 disconnected and in absence of any optically active substance in the measuring cell 12.

An oscillator 20 controls the light source 2, a frequency divider 21 and a counting circuit 22 with its output signal $U_{20}$ having a frequency $f_0$. The modulator 6 and the counting circuit 22 are controlled by the modulator frequency $f_F$ of the output signal $U_{21}$ from the frequency divider 21. One output signal $U_{22}$ from the counting circuit 22 is sent as a logical control signal for an integrator 26. An output signal $U_{16}$ from the detector 16 is fed, preferably via an amplifier 25 as input to the integrator 26. Two further output signals $U_{23}$ and $U_{24}$ from the counting circuit 22 are fed into one input of memories 27 and 28, respectively. The memories 27, 28 also have a second input which receives the output signal $U_{26}$ from the integrator 26. The memories 27 and 28 are preferably of the sample-and-hold type. The output signals $U_{27}$ and $U_{28}$ from the memories 27 and 28 are fed into a divider 30. The divider 30 further has an additional summing input. This additional input is provided with a given constant voltage $U_K$ from a constant-voltage source 29.

In operation of the embodiment of FIG. 1, the measuring cell 12 receives a liquid substance that is to be measured. It should be noted that the invention can also be used for measuring a solid substance, for example, an organic substance having asymmetric carbon bonds, or any general optically active crystal such as quartz, cinnabar, or one of the sulfuric acid double salts from the alkali metals. The solid substance would be placed in the measuring cell 12 for carrying out the measurement.

Referring to FIG. 2, there is shown a diagram plotting the output voltage $U_{20}$ from the oscillator 20 as a function of the time t. The oscillator 20 supplies a constant output frequency $f_O$.

According to the diagram of FIG. 2A, there is shown the output signal from the frequency divider 21. The output signal $U_{21}$ has a modulation frequency $f_F$ which is preferably at least one, and in particular, about two orders of magnitude smaller than the oscillator frequency $f_0$.

The photo current $U_{16}$ from the detector 16 is shown in the diagram of FIG. 2B. The diagram indicates the noise of the photo current, or the voltage $U_{16}$ proportional to the noise of the photo current, as well as the different mean amplitudes of the photo currents during both phases of the Faraday current. Using a vanishing angle of rotation $\alpha_M=0$ within the measuring cell 12 allows both amplitudes to have the same value.

After amplification of the photo current $U_{16}$ and its integration, an output signal from the integrator 26 is obtained as shown in the diagram of FIG. 2D. The output signal $U_{26}$ is reset, at times $t_3$ and $t_7$ by resetting pulses $U_{22}$ having a length $\tau_R$ from $t_3$ to $t_4$ and from $t_7$ to $t_8$ as shown in FIG. 2C.

According to the diagrams of FIGS. 2E and 2F, at times $t_1$ to $t_2$ and $t_4$ to $t_6$, the control pulses $U_{23}$ and $U_{24}$ from the counting circuit 22 alternately switch the memories 27 and 28 into the sampling state.

According to the diagrams of FIGS. 2G and 2H, the output voltages $U_{27}$ and $U_{28}$ from the memories 27 and 28 change only during corresponding sample pulses $\tau_{S+}$ and $\tau_{S-}$. The difference or the quotient Q from output voltages $U_{27}$ and $U_{28}$ furnish, after subtracting the constant volta $U_K$, the measuring signal $U_A$. The measuring angle $U_A$ is proportional to the angle of rotation $\alpha_M$ of the plane of polarization and thereby, to the concentration of the optically active substance contained in the measuring cell 12.

This embodiment of the measuring apparatus produces a resolution for the angle of rotation of the plane of polarization given by the equation:

$$\Delta \alpha_M = 5 \times (10^{-4})$$

Figure 3:
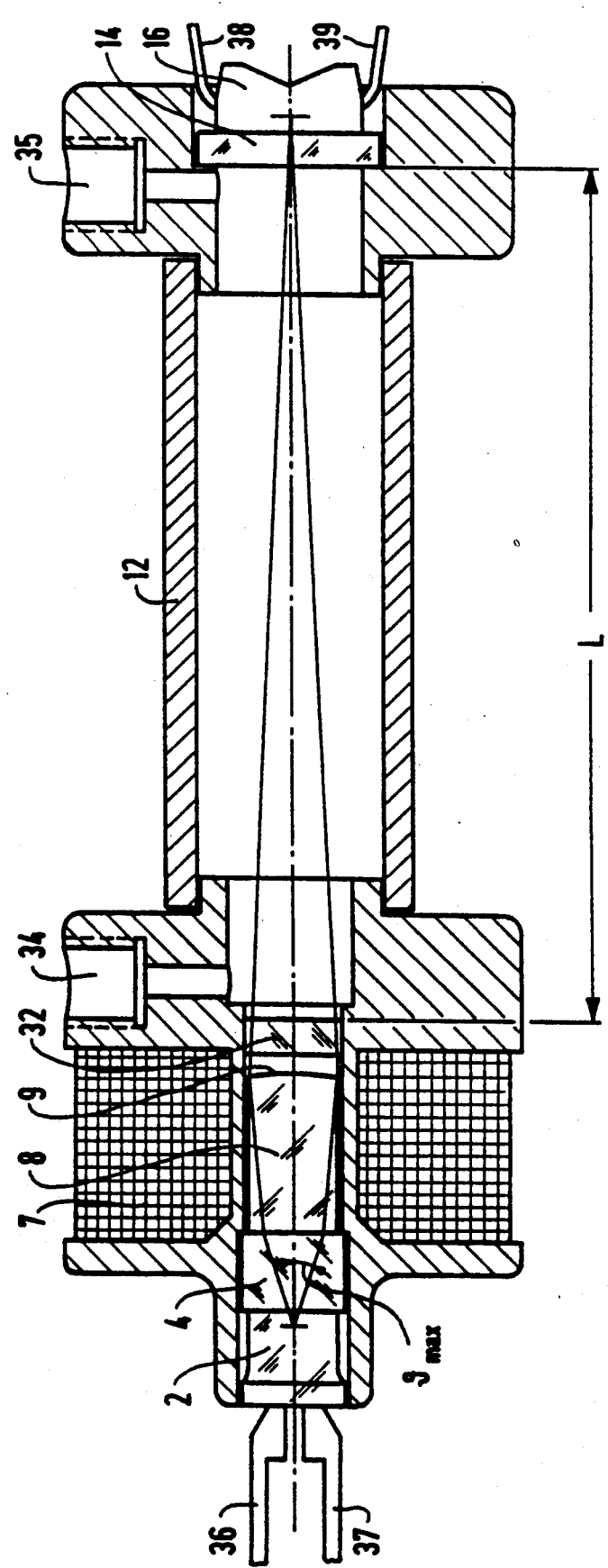
FIG. 3 shows a preferred embodiment of a polarimeter according to the invention.

Referring to FIG. 3, there is shown another embodiment for an implantable glucose measuring polarimeter. In this embodiment, the light source 2, polarizer 4 and Faraday crystal 8 are cemented to each other. Imaging of the radiating crystal surface from the light source 2 on the detector 16 is accomplished exclusively by the lens action obtained by the convex back surface 9 of the Faraday crystal 8. The transmission of the surface 9 is preferably enhanced by a $\lambda/4$ layer of silicon oxide SiO or a more highly oxidized mix of $SiO_x$ with $1<x<2$. The measuring cell 12, having a length L, for example, L=27 mm, is closed off on its input side with a window 32. The window 32 is preferably a neutral glass window. The output side of the measuring cell 12 is closed off by the analyzer 14. Two holes 34, 35 serve to allow the measuring liquid to flow through the cell 12. The liquid typically may be a filtered blood serum. Two pairs of electric terminals 36, 37 and 38, 39 are provided for coupling to the light source 2 and the detector 16, respectively. The terminals used for the Faraday coil 7 are not shown in the figure for simplification. The indicated ray bundle is limited by the maximum usable angle opening 2 $\nu_{max}$ for the radiation emitted by the light source 2.

In the embodiment of FIG. 3, in which the light source 2, the polarizer 4 and the Faraday crystal 8 are cemented together by immersion layers, practically no reflection losses are obtained. Further, a mechanically strong assembly results.

A relatively small, inexpensive and stable light source 2, preferably a light-emitting diode LED, can be provided which furnishes monochromatic radiation which can be modulated at high frequency.

Because the light source 2 can be imaged on the detector 16 through the use of lenses, the maximum amplitude of the photo current and therefore, a favorable signal-to-noise ratio, are obtained. The convex back surface 9 of the Faraday crystal 8 produces an immersion lens action with respect to the light source 2. This allows the utilization of the high index of refraction, for example, n=3.4 for gallium phosphide GaP when using a wavelength $\lambda = 575$ mm (yellow). By this means, the cost of the lenses for imagining the light source 2 on the detector can be saved altogether or at least partially reduced. A semiconductor laser diode is also suitable for use as the light source because of its high radiation output and the maximum measuring sensitivity achievable thereby.

Preferably suited for the optical medium of the Faraday crystal 8 in the modulator 6 is an $A_{III} B_V$ semiconductor crystal. These compounds have a large Verdet constant V, i.e., a strong Faraday effect is obtained with a relatively small magnetic field in the Faraday coil 7. An especially well suited compound is gallium phosphide having a Verdet constant $V = 4.5 \times 10^3$ min/(T×cm) at a wavelength $\lambda = 665$ nm and a constant $V = 6.7 \times 10^3$ min/(T×cm) for a wavelength $\lambda = 560$ nm. Preferably suited for the detector 16 is a silicon photo diode or a silicon photo cell.

It is preferable to use a garnet, which can be produced in large crystals according to the Czochralski method, IG for the optical medium of the Faraday crystal 8. The garnet should have great purity and a large Faraday constant. One such garnet has a gadolinium-gallium base. These garnets are transparent throughout the entire visible spectral range. Also highly suited are iron garnets of the type $M_3Fe_4O_{12}$, where M is one of the rare earth metals, particularly ytterbium, thulium, yttrium, erbium or holmium. These rare earth metals have a very large Faraday constant below the magnetic saturation, for example, $V = 4 \times 10^4$ min/(T×cm) for the yttrium—iron garnet ($Y_3Fe_5O_{12}$) for a wavelength of $\lambda = 1$ μm. Therefore, very short Faraday crystals 8 less than 1 mm in length can be used. The coil 7 surrounding the crystals 8 can thus be very small which again decreases the amount of electric energy required for generating the magnetic field. This is particularly important for the implantable glucose sensor, since only very-low-power supplies can be employed.

In conjunction with iron garnets, an infrared light-emitting diode of gallium-indium-arsenide-phosphide $Ga_xIn_{1-x}As_yP_{1-y}$ is preferably used as the light source. This LED has an emission wavelength in the range $0.9$ $\mu m \leq \lambda \leq 1.4$ $\mu m$ and, more preferably, in the range of $1.0$ $\mu m \leq \lambda \leq 1.11$ $\mu m$. In this range, the radiation penetration depth in water is larger than 60 mm, so that cell lengths of this order of magnitude can be employed. Thereby, correspondingly low concentrations of the optically active substance, particularly glucose, can be measured. In conjunction with iron garnets, a germanium photo diode or a germanium photocell can be employed as the detector 16, especially for wavelengths in the range $1.0$ $\mu m \leq \lambda \leq 1.7$ $\mu m$.

The Faraday coil's 7 control voltage $U_{21}$, having the modulation frequency $f_F$, is a symmetrical squarewave voltage as seen from the diagram of FIG. 2A. With this control voltage $U_{21}$, the largest possible detector signal $U_{16}$, for a given amplitude of the coil current, is obtained. The oscillator frequency $f_0$ becomes approximately $100 \times f_F$ and the modulation frequency $f_F$ is chosen $\leq 500$ Hz.

The oscillator frequency $f_0$, representing the clock frequency $f_L$ of the light source 2, is preferably chosen to be substantially larger than the modulating frequency $f_F$, as seen from the diagrams of FIGS. 2 and 2A. The modulation frequency $f_F$ is preferably chosen to be in the range $50$ Hz $\leq f_F \leq 500$ Hz. The clock frequency $f_L$ provides an increased light yield in conjunction with an LED light source 2 by utilizing the nonlinear emission-operating current characteristic of the LED, especially in the visible range of the spectrum. Thereby, an improved signal-to-noise ratio is obtained and thus a higher measuring sensitivity. Using an oscillator frequency $f_0$ as the clock frequency $f_L$ for the light source 2, the exact same number of radiation pulses from the light source 2 is obtained in each integration period without any additional circuitry cost. The integration period has a duration of $1/(2 \times f_F)$. This provides a measuring signal which is a highly stable measuring signal.

The starting times $t_1$ and $t_5$ for the sample pulse time intervals $\tau_{s+}$ and $\tau_{s-}$ of the sample-and-hold memories 27 and 28 as well as the starting times $t_3$ and $t_7$ of the resetting time intervals $\tau_R$ for the integrator 26 are determined by counting out $f_O$ and $f_L$ periods during each period $f_F$. Thereby, very accurate and equal integration times for each of the integral values to be stored in the two memories 27 and 28 are obtained.

In the method of the present invention, an output signal is obtained having low noise and drift $U_A = (U_{27}/U_{28}) \times U_N - U_K = Q - U_K$. The output signal $U_A$ is zero by a suitable choice of the constant voltage $U_K$ at a zero or background angle of rotation of the polarization plane in the measuring cell 12. The output signal is thus proportional as a measure for the desired concentration of the optically active substance to the angle of rotation $\Delta \alpha_M$ caused by this substance. Therefore, $U_A \sim \Delta \alpha_M$. $U_N$ is the constant internal normalizing voltage of the divider 30.

The primary measurement signal is the photo current $i_{ph}$ generated in the detector 16. The principal passage directions of the polarizer 4 and the analyzer 14 are perpendicular to each other, i.e., they are adjusted for minimum transmission. The direction of vibration corresponding to the situation when the polarized radiation strikes the analyzer 14 is characterized by the angle of rotation $\alpha = 0$ for the plane of vibration. The plane of polarization of the radiation leaving the polarizer 4 is alternately rotated the maximum angles $\pm \alpha_F$ of the same magnitude, by the a-c current of the frequency $f_F$ flowing through the Faraday coil 7. In the cell 12, the optically active substance causes a further rotation by the angle $\alpha_M$ proportional to the concentration C of the substance. Thereby, the photo current $i_{ph}$ oscillates with the frequency $f_F$ between a minimum value depending on the degree of polarization and the alternately generated extreme values as shown by Eq. (1).

$$i_{ph\pm} = \sin^2(\pm \alpha_F + \alpha_M) + i_u \times \cos^2(\pm \alpha_F \pm \alpha_M) = i_u + (i_o - i_u) \times \sin^2(\pm \alpha_F + M). \quad \text{Eq. (1)}$$

With an alternating squarewave current in the Faraday coil 7, only the values $i_{ph+}$ and $i_{ph-}$ are alternately generated.

An ideal case has completely linear polarization of the radiation reaching the analyzer 14. In this case, the "depolarization component" $i_u = 0$. When the Faraday modulator 6 is turned off and the optically active substance in the measuring cell 12 is absent, i.e., with $\alpha_F = \alpha_M = 0$, then the photo current $i_{ph}$ disappears.

Figure 4:
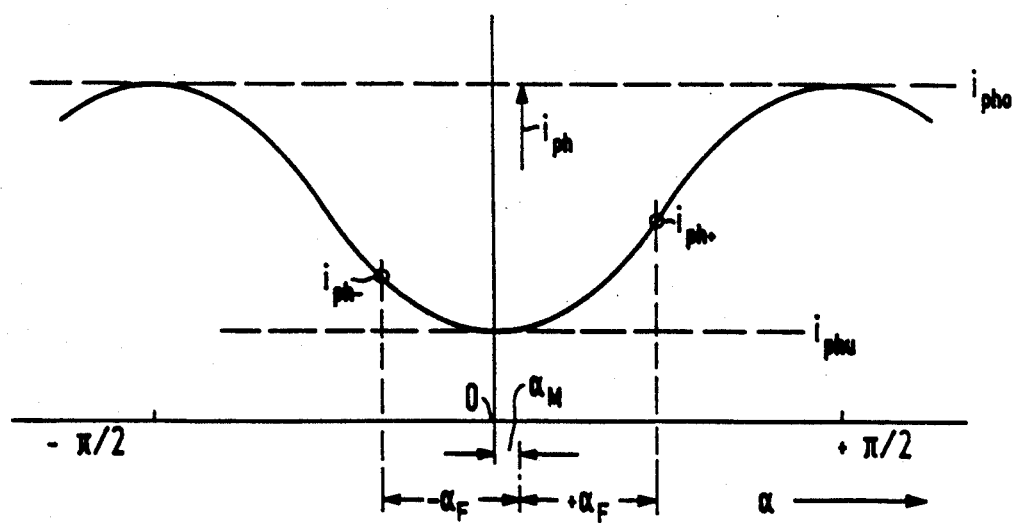
FIG. 4 is a diagram showing the photo current waveform as a function of the measured angle and the modulation angle.

For the general case of incomplete polarization $0 < i_u < i_o$, the formation of the total current $U_{16}$, having different amplitudes $i_{ph+}$ and $i_{ph-}$, is shown in FIG. 4. The depolarization component $i_u$ is shown exaggerated such that $i_u = i_o/4$. With commercially available polarizers, $i_u$ can be less than $i_o/100$. If the ratio:

$$\epsilon = i_u/i_o = (1-p) \quad \text{Eq. (2)}$$

of Eq. (2) is introduced as a measure for the degree of polarization p of the radiation reaching the detector 16, then Eq. (1) for the two photo currents which are generated by the Faraday coil 7, assume the following form:

$$i_{ph\pm} = i_o[\epsilon + (1-\epsilon) \times \sin^2(\pm \alpha_F + \alpha_M)]. \quad \text{Eq. (3)}$$

The photo current $i_{ph}$ is amplified in the amplifier 25 to form the voltage $U_v = v \times i_{ph}$ and is subsequently integrated by integrator 26 to form the two voltages $$U_{I\pm} = \frac{1}{R_J \times C_J} \times \int_0^{2J} U_{v\pm} dt = \frac{\tau_J}{R_J \times C_J} \times \overline{U}_{v\pm} \quad \text{Eq. (4)}$$

where $\tau_J$ is the effective integration time. $\tau_J$ is fixed by the oscillator 20, the frequency divider 21 and the counting circuit 22 and is equal to the time difference $t_5 - t_4$ between the end of a resetting pulse $U_{22}$ at time $t_4$ and the next following storage pulse $U_{24}$ at time $t_5$. The integrator 26 acts in a manner known per se as a mean value amplifier having adjustable gain.

The integral values $U_{I\pm}$ of alternately generated voltage $U_{26}$ are stored separately during the time intervals $\tau_{s+}$ and $\tau_{S-}$ defined by the voltage pulses $U_{23}$ and $U_{24}$. The changing contents of the memory and the additive constant voltage $U_K$ from the constant voltage source 29, allows the output voltage $(U_A)$ to be finally generated in the divider 30 as follows:

$$U_A = \frac{U_I^+}{U_I^-} \times U_N - U_K = \frac{\overline{i}_{ph+}}{\overline{i}_{ph-}} \times \quad \text{Eq. (5)}$$

-continued
$$U_N - U_K = \frac{U_{27}}{U_{28}} \times U_N - U_K$$

The bars over $i_{ph+}$ and $i_{ph-}$ in Eq. (5) indicate that each of the two photo currents are averaged over the corresponding period $\tau_J$. $U_N$, as mentioned above, is the internal normalizing voltage of the divider 30, for example, 10 V. If the constant voltage $U_K$ is set equal to the internal normalizing voltage $U_N$, then one obtains:

$$U_A = \left(\frac{\overline{i_{ph+}}}{\overline{i_{ph-}}} - 1\right) \times U_N \qquad \text{Eq. (6)}$$

With the photo current calculated in accordance with Eq. (3), or the voltage $U_{16}$ proportional thereto, the output signal normalized to the voltage $U_N$ is as follows:

$$y = \frac{U_A}{U_N} = \frac{(1 - \epsilon) \times \sin 2\alpha_M \times \sin 2\alpha_F}{\epsilon + (1 - \epsilon) \times \sin^2(\alpha_M - \alpha_F)} \qquad \text{Eq. (7)}$$

Similar to the integration of Eq. (4), the variables $\alpha_M$, $\alpha_F$ and $\epsilon$ on the right side of Eq. (7) are interpreted as mean values over an integration period $\tau_J$. Thereby, the output voltage $U_A$ and the normalized output signal $y$ are also mean values having a corresponding reduced noise component. For a further reduction of the noise bandwidth, the divider 30 is preferably chosen to have a time constant $\tau_Q > 1/f_F$.

For the case of small rotations in the plane of polarization (this is particularly important for determining glucose concentration) and a small Faraday rotation $\sin \alpha_F << 1$, for example, $\alpha_F = 2°$, $\sin \alpha_F = 0.035$, then Eq. (7) simplifies to:

$$y = 4 \times \frac{\alpha_M}{\alpha_F} \times \left(1 - \frac{1}{1 + \left(\frac{1}{\epsilon} - 1\right) \times \alpha_F^2}\right) \qquad \text{Eq. (8)}$$

In addition, if the radiation is linearly polarized to a sufficient degree, such that:

$$\epsilon = \frac{i_u}{i_o} << \frac{1}{1 + 1/\alpha_F^2} \qquad \text{Eq. (9)}$$

then the fractional term in Eq. (8) can be neglected and the output signal becomes proportional to the angle of rotation $\alpha_M$ and therefore also to the concentration C of the optically active substance to be measured as shown by Eqs. (10) and (11), respectively.

$$y = 4 \times \alpha_M/\alpha_F \qquad \text{Eq. (10)}$$
$$U_A = 4 \times (\alpha_M/\alpha_F) \times U_N \qquad \text{Eq. (11)}$$

According to the different possible algebraic representations of Eq. (5), as for example, shown in Eq. (5A)

$$U_A = (U_{27} - U_{28}) \times \frac{U_N}{U_{28}} + U_N - U_K = \qquad \text{Eq. (5A)}$$

-continued
$$(U_{27} - U_{28}) \times \frac{U_N}{U_{28}} + \delta U_A$$

the output voltage $U_A$ can also be determined from the two output signals $U_{27}$ and $U_{28}$ in a manner known per se by a subtraction and subsequent division. Accurate adjustment of the null point for compensating small deviations between the photo currents $\overline{i_{ph+}}$ and $\overline{i_{ph-}}$ or between the output signals $U_{27}$ and $U_{28}$ only requires the addition of a small offset voltage $\gamma U$ $\gamma U_A = U_N - U_K$ when adjusting the analyzer 14 for minimum transmission. Therefore, the output circuitry of the two sample and hold memories 27 and 28 in FIG. 1 can also be represented by an equivalent circuit diagram as shown in FIG. 5.

Figure 5:
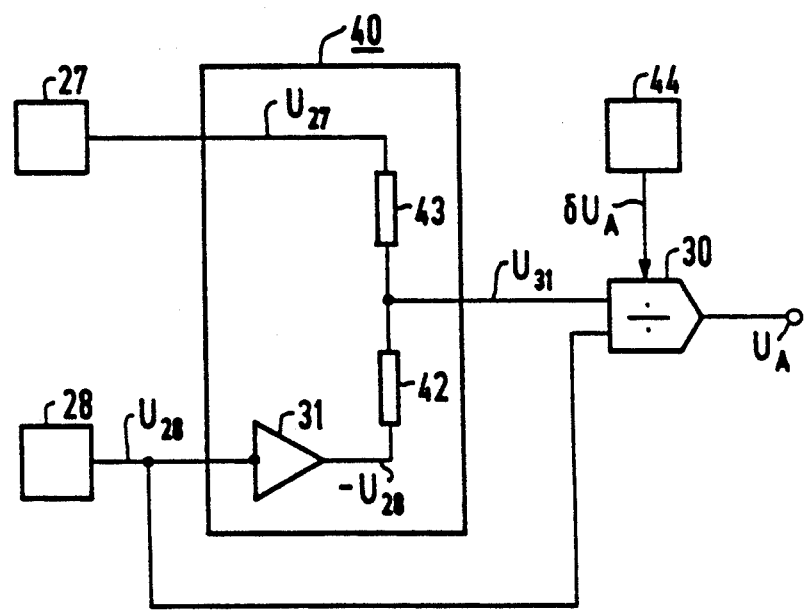
FIG. 5 schematically illustrates an embodiment of the two memory contents in the processor of the present invention.

In the circuit of FIG. 5, the difference voltage $U_{31} = (U_{27} - U_{29})/2$ is formed in the subtractor 40. The subtractor 40 can include, for example, an inverter 31 and two resistors 42 and 43. Subsequently, the difference voltage $U_{31}$ is divided by the output signal $U_{28}$ in a divider 30, taking into consideration the factor 2. The constant-voltage source 44 only needs to supply the small offset voltage $\gamma U_A$, which for an ideal adjustment equals zero.

In the embodiment according to FIG. 1, an analog signal processor is provided. The functional elements, shown in the lower part of FIG. 1 however, can partially be replaced, for example, by a microprocessor. The microprocessor would function as the oscillator 20, the frequency divider 21, the counting circuit 22 as well as the integrator 26, the sample-and-hold memories 27 and 28 and the divider 30 having the constant-voltage source 29.

Further the embodiment according to FIG. 1 provides a Faraday modulator as the modulator 6. In some cases it may be advantageous to use a Kerr modulator in which an artificial birefringence is generated. Thereby, a rotation of the plane of polarization by the electric field strength also occurs.

What is claimed is:
1. In a system including a light source, a modulator operated at a predetermined modulation frequency, an analyzer and a detector, a method for measuring the concentration of optically active substances comprising the steps of:
  (a) measuring with said detector the polarization of light fed through said substances to produce an output signal;
  (b) alternately integrating the output signal from the detector, during each half period of said modulation frequency, to first and second voltage values, respectively;
  (c) storing said first and second voltage values;
  (d) forming a quotient from the first and second stored voltage values; and
  (e) subtracting an adjustable constant voltage from said quotient.
2. A method according to claim 1 further comprising the step of generating the modulation frequency by frequency division of an oscillator frequency.
3. A method according to claim 2 wherein the oscillator frequency is approximately one hundred times the modulation frequency and the modulation frequency is between 50 and 500 Hz.
4. A method according to claim 1 further comprising the step of clocking the operation of the light source with a clock frequency substantially higher than the modulation frequency.

5. A method according to claim 4 wherein the oscillator frequency is the clock frequency.

6. A method according to claim 1 wherein the measuring step further comprises the step of amplifying the output signal from the detector.

7. A method according to claim 1 wherein said integrating and storing steps further comprise the steps of counting the period of the oscillator frequency during each period of the modulation frequency; and
determining starting times for reset and sample and hold pulses used in the integrating and storing steps.

8. A method according to claim 1 wherein said integrating and storing steps further comprise the steps of counting the period of the clock frequency during each period of the modulation frequency; and
determining starting times for reset and sample and hold pulses used in the integrating and storing steps.

9. An apparatus for measuring the concentration of optically active substances by measuring the polarization of light fed through said substances, the apparatus comprising:
 (a) a measuring cell for holding said substances;
 (b) a light source requiring a clock frequency for providing the light which is fed through said substances;
 (c) a modulator coupled between the light source and one end of the measuring cell for modulating the light from the light source, said modulator having a modulation frequency;
 (d) an analyzer coupled to the opposite end of the measuring cell;
 (e) a detector coupled to said analyzer for receiving the light fed through said substances to provide a first output signal;
 (f) an integrator coupled to the output of said detector for producing a second output signal;
 (g) a first and a second memory for alternately storing said second output signal;
 (h) a divider having inputs for receiving the contents of said first and second memories and having an additional input;
 (i) a constant voltage source coupled to said additional input of the divider;
 (j) an oscillator having an oscillator frequency providing the clock frequency to the light source;
 (k) a frequency divider, controlled by said oscillator frequency, for generating the modulation frequency; and
 (l) a counting circuit receiving the modulation frequency and the oscillator frequency, said counting circuit further including time delay stages for controlling a plurality of pulse voltages, a separate one of said pulse voltages being fed to the integrator, and said first and second memories.

10. An apparatus according to claim 9 wherein the first and second memories are sample-and-hold memories, the apparatus further comprising a subtractor coupled to said sample-and-hold memories; said subtractor further coupled as one input to the divider.

11. An apparatus according to claim 1 wherein the modulator is a Faraday modulator.

12. An apparatus according to claim 9 wherein the divider forms a quotient, said additional input to the divider having a time constant $\tau_Q > 1/f_F$.

13. An apparatus according to claim 9 wherein the light source is a light-emitting diode (LED).

14. An apparatus according to claim 9 wherein the light source is a semiconductor laser diode.

15. An apparatus according to claim 11 wherein the modulator contains a Faraday crystal having an $A_{III}B_V$ compound.

16. An apparatus according to claim 15 wherein the Faraday crystal is made of gallium phosphide GaP.

17. An apparatus according to claim 14 wherein the Faraday crystal is made of gallium arsenid GaAs.

18. An apparatus according to claim 11 wherein the modulator contains a Faraday crystal of an $A_{1III}A_{2III}(1-x)^{B1}V y^{B2}V(1-y)$ compound, in which $0 \leq (x,y) \leq 1$.

19. An apparatus according to claim 9 wherein the detector is a silicon photo diode.

20. An apparatus according to claim 19 wherein the silicon photo diode is a silicon PIN photo diode.

21. An apparatus according to claim 9 wherein the detector is a photo cell.

22. An apparatus according to claim 9 wherein the detector is a photo transistor.

23. An apparatus according to claim 11 further comprising a polarizer, said light source, polarizer, and Faraday crystal being coupled to each other by immersion layers.

24. An apparatus according to claim 9 further comprising a plurality of lenses for imaging the light source onto the detector.

25. An apparatus according to claim 11 wherein the Faraday modulator includes a Faraday crystal having a convex back surface.

26. An apparatus according to claim 11 wherein a garnet is provided as the Faraday crystal.

27. An apparatus according to claim 26 wherein the garnet has a gadolinium-gallium base.

28. An apparatus according to claim 26 wherein the garnet characterized is an iron garnet of the type $M_3Fe_5O_{12}$, in which M is one of the rare earth metals.

29. An apparatus according to claim 28 wherein M is ytterbium Yb.

30. An apparatus according to claim 28 wherein M is thulium Tm.

31. An apparatus according to claim 28 wherein M is yttrium Y.

32. An apparatus according to claim 28 wherein M is erbium Er.

33. An apparatus according to claim 28 wherein M is holmium Ho.

34. An apparatus according to claim 28 wherein the light source is an infrared light-emitting diode made of $Ga_xIn_{1-x}As_yP_{1-y}$ and having an emission wavelength $\lambda$ in the range $0.9 \, \mu m \leq \lambda \leq 1.4 \, \mu m$.

35. An apparatus according to claim 29 wherein the emission wavelength $\lambda$ is in the range of $1 \, \mu m \leq \lambda \leq 1.11 \, \mu m$.

36. An apparatus according to claim 29 wherein the detector is made of a germanium photo diode.

37. An apparatus according to claim 29 wherein the detector is made of a germanium photocell.

38. An apparatus according to claim 9 wherein the modulation frequency control voltage is a symmetrical squarewave voltage.

* * * * *